United States Patent
Ci

(10) Patent No.: US 10,576,120 B2
(45) Date of Patent: Mar. 3, 2020

(54) CHINESE HERBAL ORAL PASTE FOR CONDITIONING QI DEFICIENCY CONSTITUTION AND PROCESSING METHOD THEREFOR

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/967,114

(22) Filed: Apr. 30, 2018

(65) Prior Publication Data

US 2019/0192604 A1    Jun. 27, 2019

(30) Foreign Application Priority Data

Dec. 26, 2017 (CN) .......................... 2017 1 1429040

(51) Int. Cl.
| | | |
|---|---|---|
| A61K 36/00 | (2006.01) |
| A61K 36/752 | (2006.01) |
| A61K 9/00 | (2006.01) |
| A61K 36/076 | (2006.01) |
| A61K 36/484 | (2006.01) |
| A61K 36/481 | (2006.01) |
| A61K 36/232 | (2006.01) |
| A61K 36/89 | (2006.01) |
| A61K 36/185 | (2006.01) |
| A61K 36/537 | (2006.01) |
| A61K 36/896 | (2006.01) |
| A61K 36/8965 | (2006.01) |
| A61K 36/8969 | (2006.01) |
| A61K 36/8945 | (2006.01) |
| A61K 36/9064 | (2006.01) |
| A61K 36/074 | (2006.01) |
| A61K 36/725 | (2006.01) |
| A61K 36/575 | (2006.01) |
| A61K 36/8967 | (2006.01) |
| A61K 36/8994 | (2006.01) |
| A61K 36/36 | (2006.01) |

(52) U.S. Cl.
CPC .......... *A61K 36/752* (2013.01); *A61K 9/0053* (2013.01); *A61K 36/074* (2013.01); *A61K 36/076* (2013.01); *A61K 36/185* (2013.01); *A61K 36/232* (2013.01); *A61K 36/36* (2013.01); *A61K 36/481* (2013.01); *A61K 36/484* (2013.01); *A61K 36/537* (2013.01); *A61K 36/575* (2013.01); *A61K 36/725* (2013.01); *A61K 36/89* (2013.01); *A61K 36/896* (2013.01); *A61K 36/8945* (2013.01); *A61K 36/8965* (2013.01); *A61K 36/8967* (2013.01); *A61K 36/8969* (2013.01); *A61K 36/8994* (2013.01); *A61K 36/9064* (2013.01)

(58) Field of Classification Search
None
See application file for complete search history.

*Primary Examiner* — Qiuwen Mi

(74) *Attorney, Agent, or Firm* — Novick, Kim & Lee, PLLC; Allen Xue

(57) ABSTRACT

A Chinese herbal oral paste includes the following components: heterophylly falsestarwort root, dangshen (*Codonopsis pilosula*), fuling, prepared liquorice root, root and vine of manyprickle acanthopanax6-18 parts of milkvetch root, dried tangerine peel, angelical-8 parts of Chinese arborvitae kernel, lotus seeds, radix asparagi, danshen root, solomonseal rhizome, hyacinth bean, Chinese yam, villous amomum fruit, coix seed, glossy ganoderma, finger citron, Chinese dates, fruit of Chinese magnoliavine, lilium brownii, xylitol, and donkey-hide gelatin. The Chinese herbal oral paste of the present disclosure has a higher drug concentration and good taste, is particularly suitable for health preserving in winter and conditioning the qi deficiency constitution, will not create negative effects or harm to the human body at all, and is capable of achieving certain efficacy of strengthening physical health.

20 Claims, 1 Drawing Sheet

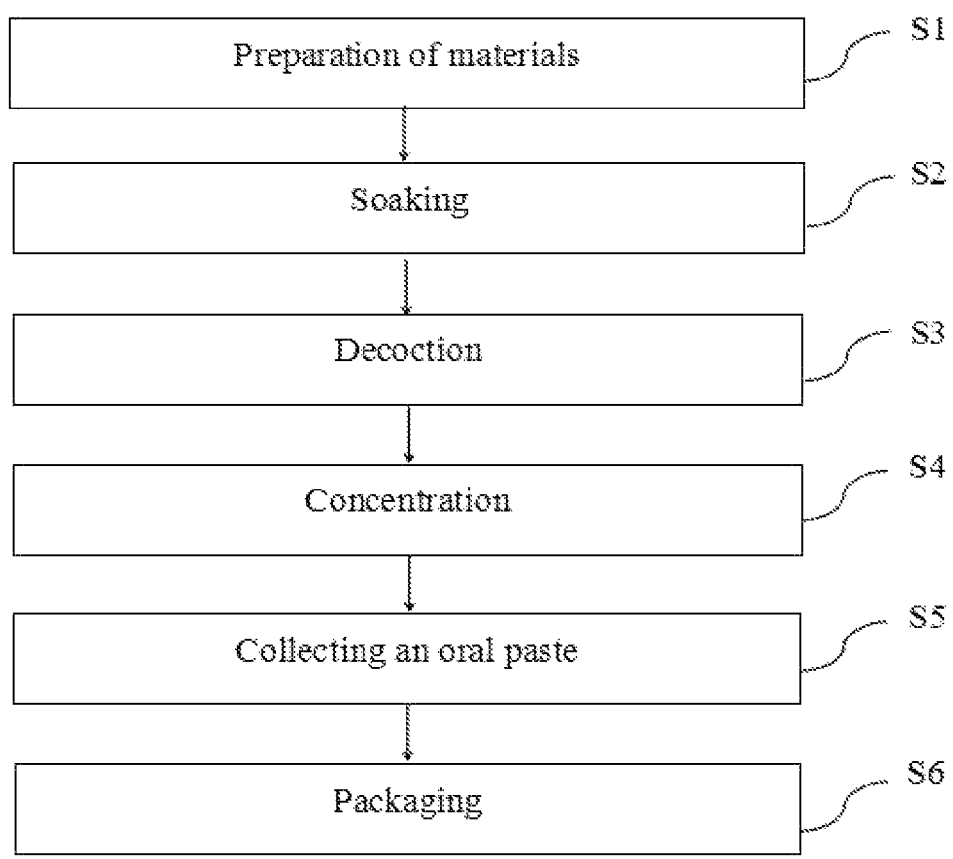

CHINESE HERBAL ORAL PASTE FOR CONDITIONING QI DEFICIENCY CONSTITUTION AND PROCESSING METHOD THEREFOR

TECHNICAL FIELD

The present disclosure relates to the field of health foods, and particularly to a Chinese herbal oral paste for conditioning qi deficiency constitution and a processing method therefor.

BACKGROUND

In Classification and Determination of Constitution in Traditional Chinese Medicine, the China Association of Chinese Medicine classifies body constitutions of the human body into nine types, including yin-yang harmony constitution, yang deficiency constitution, yin deficiency constitution, qi deficiency constitution, phlegm-dampness constitution, damp-heat constitution, qi depression constitution, blood stasis constitution, and allergic constitution, most of which belong to sub-healthy states.

The qi deficiency constitution means that, when internal organs of the human body are dysfunctional and transformation and generation of qi are insufficient, manifestations of qi deficiency would easily occur, which are usually represented by faint low voice, emaciation of the body or overweight, pale complexion, shortness of breath and unwillingness to speak, lassitude, body fatigue and weakness, spontaneous perspiration which is especially more serious when in movement, pale red tongue with teeth prints and with white tongue coating, and weak pulse, diseases are caused due to various causes, different symptoms are seen due to the difference in qi-deficient parts such as heart, lung, spleen and kidney. The tendency of morbidity is: being susceptible to common cold and visceroptosis, usually having weakened immune systems and having slow recovery from illness. For this, qi tonifying and qi nourishing are taken as the general therapeutic principle, and prescriptions for tonifying viscera are selected on the basis of differentiation of diseases according to pathological changes of the viscera and their interrelations.

The qi deficiency constitution is formed mainly because native endowment is deficient and after long-term eating disorder, emotional disorder, long illness and fatigue, oldness and weakness cause heart, lung, spleen and kidney damages. Since heart governs blood and vessels, lung dominates qi throughout the body, kidney stores vigor, and spleen and stomach are "source of engendering transformation of qi", the qi deficiency constitution will easily develop symptoms that the effect of promoting blood running is reduced, transformation and generation of qi in the body are insufficient, and the functions of the body in preventing the invasion of exogenous pathogenic factors, protecting the superficies of the body, and maintaining the positions of the internal organs are decreased.

It is mentioned in the Inner Canon of the Yellow Emperor that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and susceptibility to diseases. It is believed in the traditional Chinese medicine that since the human beings live in the natural world, physiological functions of the human body usually change with seasons, that is, "correspondence between man and nature". Winter is the season when the human body "stores energies", thus appropriate nourishment can enhance the constitution, ward off diseases and strengthen the body, and prolong life, that is, conditioning in winter or nourishing in winter commonly mentioned in the traditional Chinese medicine. For the sub-healthy population with qi deficiency constitution, a solid oral paste with a higher drug concentration and good taste, and being convenient to carry more meets requirements of modern people.

SUMMARY

A main object of the present disclosure is to provide a Chinese herbal nourishing product suitable for conditioning in winter so as to treat qi deficiency constitution.

In order to achieve the above object, according to one aspect of the present disclosure, there is provided a Chinese herbal oral paste for conditioning qi deficiency constitution.

The Chinese herbal oral paste for conditioning qi deficiency constitution according to the present disclosure includes the following components in parts by weight: 5-16 parts of heterophylly falsestarwort root, 4-15 parts of dangshen (*Codonopsis pilosula*), 5-16 parts of fuling, 3-7 parts of prepared liquorice root, 6-17 parts of root and vine of manyprickle acanthopanax, 6-18 parts of milkvetch root, 3-9 parts of dried tangerine peel, 2-14 parts of angelica, 2-8 parts of Chinese arborvitae kernel, 7-17 parts of lotus seeds, 5-16 parts of radix asparagi, 5-16 parts of danshen root, 6-17 parts of solomonseal rhizome, 7-15 parts of hyacinth bean, 6-20 parts of Chinese yam, 1-5 parts of villous amomum fruit, 3-17 parts of coix seed, 6-18 parts of glossy ganoderma, 3-10 parts of finger citron, 5-14 parts of Chinese dates, 3-9 parts of fruit of Chinese magnoliavine, 13-25 parts of lilium brownii, 20-40 parts of xylitol, and 30-50 parts of donkey-hide gelatin.

Furthermore, the Chinese herbal oral paste for conditioning qi deficiency constitution according to the present disclosure includes the following components in parts by weight: 7-13 parts of heterophylly falsestarwort root, 7-13 parts of dangshen (*Codonopsis pilosula*), 7-13 parts of fuling, 4-6 parts of prepared liquorice root, 9-14 parts of root and vine of manyprickle acanthopanax, 9-15 parts of milkvetch root, 5-7 parts of dried tangerine peel, 6-10 parts of angelica, 4-7 parts of Chinese arborvitae kernel, 10-15 parts of lotus seeds, 7-13 parts of radix asparagi, 7-13 parts of danshen root, 9-13 parts of solomonseal rhizome, 10-13 parts of hyacinth bean, 10-16 parts of Chinese yam, 2-4 parts of villous amomum fruit, 9-15 parts of coix seed, 9-15 parts of glossy ganoderma, 5-7 parts of finger citron, 7-13 parts of Chinese dates, 5-7 parts of fruit of Chinese magnoliavine, 16-23 parts of lilium brownii, 25-35 parts of xylitol, and 35-45 parts of donkey-hide gelatin.

Furthermore, the Chinese herbal oral paste for conditioning qi deficiency constitution according to the present disclosure includes the following components in parts by weight: 10 parts of heterophylly falsestarwort root, 10 parts of dangshen (*Codonopsis pilosula*), 10 parts of fuling, 5 parts of prepared liquorice root, 12 parts of root and vine of manyprickle acanthopanax, 12 parts of milkvetch root, 6 parts of dried tangerine peel, 8 parts of angelica, 6 parts of Chinese arborvitae kernel, 12 parts of lotus seeds, 10 parts of radix asparagi, 10 parts of danshen root, 12 parts of solomonseal rhizome, 12 parts of hyacinth bean, 13 parts of Chinese yam, 3 parts of villous amomum fruit, 12 parts of coix seed, 12 parts of glossy ganoderma, 6 parts of finger citron, 10 parts of Chinese dates, 6 parts of fruit of Chinese magnoliavine, 20 parts of lilium brownii, 30 parts of xylitol, and 40 parts of donkey-hide gelatin.

In order to achieve the above object, according to the other aspect of the present disclosure, there is a processing method for a Chinese herbal oral paste for conditioning qi deficiency constitution.

The processing method for a Chinese herbal oral paste for conditioning qi deficiency constitution according to the present disclosure includes the following steps in sequence: preparation of materials, soaking, decoction, concentration, and collecting an oral paste.

Furthermore, the step of preparation of materials is: measuring raw materials of formula ratio according to composition of the Chinese herbal oral paste, and washing raw materials, except donkey-hide gelatin and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by stirring while decocting and concentrating with low heat, until the drug liquid does not disperse when being dropped on paper, to obtain a vegetarian paste.

Furthermore, the step of collecting an oral paste is: pouring xylitol and melted donkey-hide gelatin into the vegetarian paste respectively, stirring them continuously with a shovel while cooking them slowly with low heat, until the juice can coagulate and not disperse into beads when dropped into clear water, then canning the resulted oral paste.

The melting step is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

The Chinese herbal oral paste of the present disclosure has a higher drug concentration and good taste, is particularly suitable for health preserving in winter and conditioning the qi deficiency constitution, will not create negative effects or harm to the human body at all, and is capable of achieving certain efficacy of strengthening physical health.

BRIEF DESCRIPTION OF THE DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing, FIG. 1 is a flow chart of a processing technology for a Chinese herbal oral paste of an embodiment of the present disclosure.

DETAILED DESCRIPTION OF THE EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

The present disclosure provides a Chinese herbal oral paste for conditioning qi deficiency constitution, including the following components: heterophylly falsestarwort root, dangshen (*Codonopsis pilosula*), fuling, prepared liquorice root, root and vine of manyprickle acanthopanax, milkvetch root, dried tangerine peel, angelica, Chinese arborvitae kernel, lotus seeds, radix asparagi, danshen root, solomonseal rhizome, hyacinth bean, Chinese yam, villous amomum fruit, coix seed, glossy ganoderma, finger citron, Chinese dates, fruit of Chinese magnoliavine, lilium brownii, xylitol, and donkey-hide gelatin.

Heterophylly falsestarwort root is sweet and slightly bitter in flavor and neutral in nature, acts on spleen and lung, replenishes qi to tonify spleen, generates body fluid and moistens lung, and is used for spleen-deficiency body tiredness, poor appetite, weakness after illness, qi and yin insufficiency, spontaneous perspiration and mouth thirst, and lung-dryness dry cough.

Tangshen is sweet in flavor and neutral in nature, acts on spleen and lung, nourishes the middle energizer and supplements qi, harmonizes stomach and promotes the secretion of body fluid, eliminates phlegm and relieves cough, and is used for reduced spleen-deficiency appetite and loose stool, numbness of limbs, palpitation, short of breath, mouth dryness, spontaneous perspiration, rectocele, and prolapse of the uterus.

Fuling is sweet and light in flavor and neutral in nature, acts on heart, lung, spleen, and kidney, alleviates water retention and clears dampness, tonifies spleen, calms the mind, and is used for edema and scanty urine, phlegm and fluid retention and dizziness and palpitation, reduced spleen-deficiency appetite, loose stool and diarrhea, uneasiness, and palpitation to insomnia.

Prepared liquorice root is sweet in flavor and neutral in nature, acts on heart, lung, spleen, and stomach, nourishes spleen and harmonizes stomach, supplements qi and restores pulse, and is used for spleen and stomach weakness, tiredness, palpitation, and irregular pulse.

Root and vine of manyprickle acanthopanax are acrid and slightly bitter in flavor and warm in nature, acts on spleen, kidney, and heart, tonifies kidney and waist, supplements qi to calm mind, promotes blood circulation to remove meridian obstruction, and is used for kidney-deficiency body weakness, soreness and weakness of waist and knees, retardation in walking of infants, spleen-deficiency asthenia, qi-deficiency edema, poor appetite, insomnia and dreamful sleep, amnesia, chest obstruction and pain, wind-cold-dampness arthralgia, and traumatic gall.

Milkvetch root is sweet in flavor and slightly warm in nature, acts on lung, spleen, liver, and kidney, tonifies defensive-qi and secures the exterior, replenishes qi and invigorates yang, draws toxin and promotes tissue generation, alleviates water retention and relieves swelling, and is used for qi-deficiency lassitude, reduced appetite and loose stool, sinking of middle qi, rectocele due to chronic diarrhea, spontaneous perspiration and night sweating, blood-deficiency etiolation, dorsal furuncle borderless swelling, phlegm-dampness edema, and internal-heat consumptive thirst.

Dried tangerine peel is bitter and acrid in flavor and warm in nature, acts on lung and spleen, regulates qi and tonifies spleen, dries dampness and resolves phlegm, and is used for abdominal fullness and distention, reduced appetite and vomiting, and cough with excessive phlegm.

Angelica is sweet and acrid in flavor and warm in nature, acts on liver, heart, and spleen, replenishes blood and invigorates the circulation of blood, regulates menstruation and relieves pain, relaxes bowel, and is used for blood-deficiency etiolation, vertigo and palpitation, irregular menstruation, amenorrhea and dysmenorrhea, deficiency-cold stomachache, rheumatic arthralgia, traumatic injury, ulcer and skin and external diseases, and constipation due to intestinal dryness.

Chinese arborvitae kernel is sweet in flavor and neutral in nature, acts on heart, kidney, and large intestine, tranquilizes the spirit by nourishing heart, relaxes bowel, resists sweating and is used for yin blood insufficiency, dysphoria and insomnia, palpitation, constipation due to intestinal dryness, and yin-deficiency night sweating.

Lotus seeds are sweet and astringent in flavor and neutral in nature, act on the spleen, kidney and heart, tonify the spleen and cures diarrhea, arrest morbid leukorrhea, tonify kidney and arrest seminal emission, nourish the heart and calm the nerves, and are used for spleen-deficiency diarrhea, morbid leukorrhea, gonobolia, and palpitation and insomnia.

Radix asparagi is sweet and bitter in flavor and cold in nature, acts on lung and kidney, nourishes yin and moistens dryness, clears lung and promotes the secretion of body fluid, and is used for lung-dryness dry cough, pertussis and sticky phlegm, soreness and ache of waist and knees, steaming bone hectic fever, internal heat consumptive thirst, febrile disease and body fluid impairment, throat dryness and thirst, and constipation due to intestinal dryness.

Danshen root is bitter in flavor and slightly cold in nature, acts on heart and liver, invigorates blood circulation to remove blood stasis, induces menstruation to stop pain, clears away the heart fire and relieves restlessness, cools blood to resolve carbuncle, and is used for chest stuffiness and pains, abdominal fullness and hypochondriac pain, mass in abdomen, heat arthralgia pain, dysphoria insomnia, irregular menstruation, dysmenorrhea and amenorrhea, and swelling pain of skin and external diseases.

Solomonseal rhizome in sweet in flavor and neutral in nature, acts on spleen, lung, and kidney, replenishes qi and nourishes yin, tonifies spleen, moistens lung, invigorates kidney, and is used for qi deficiency of spleen and stomach, body tiredness and lassitude, stomach yin insufficiency, mouth dryness and reduced appetite, lung-deficiency dry cough, over-strained cough and hemoptysis, essence and blood insufficiency, soreness and weakness of waist and knees, premature graying of hair, and internal-heat consumptive thirst.

Hyacinth bean is sweet in flavor and slightly warm in nature, acts on spleen and stomach, invigorates spleen to eliminate dampness, and is used for splenasthenic diarrhea, morbid leukorrhea and vomiting and diarrhoea caused by summer-heat dampness.

Chinese yam is sweet in flavor, neutral in nature, and non-toxic, acts on spleen, lung, and kidney, strengthens spleen and stomach, nourishes lung qi, tonifies kidney essence, nourishes physical health, renders good hearing and eyesight and delays senility upon long administration, and is used for reduced spleen-deficiency appetite, loose stool diarrhea, lung-deficiency asthma, gonobolia and frequent urination, and yin-deficiency consumptive thirst.

Villous amomum fruit is acrid in flavor and warm in nature, acts on spleen, stomach, and kidney, promotes the circulation of qi to regulate middle energizer, harmonizes stomach, refreshes spleen, and is used for abdominal pain and distension, anorexia and dyspepsia, dysphagia and vomiting, cold diarrhea and dysentery, and fetal movement.

Coix seed is sweet and light in flavor and cool in nature, acts on spleen, stomach, and lung, alleviates water retention and clears dampness, tonifies spleen and cures diarrhea, eliminates arthralgia syndromes, discharges pus, clears away toxic matters and removes stasis, and is used for edema, beriberi, difficult urination, spleen-deficiency diarrhea, dampness arthralgia muscular constriction, pulmonary abscess, intestinal carbuncle, excrescence, and cancerous protuberance.

Glossy ganoderma is sweet in flavor and neutral in nature, acts on liver, lung, and kidney, supplements qi to calm mind, relieves cough and asthma, and is used for vertigo and insomnia, palpitation and shortness of breath, and consumptive asthma.

Finger citron is acrid, bitter, and sour in flavor, and warm in nature, acts on liver, spleen, stomach, and lung, soothes liver and regulates qi, harmonizes stomach to relieve pain, dries dampness and eliminates phlegm, and is used for qi-stagnation in liver and stomach, distending pain in chest and hypochondrium, stomach distention and fullness, reduced appetite and vomiting, and cough with excessive phlegm.

Chinese date are sweet in flavor and warm in nature, acts on spleen and stomach, nourishes the middle energizer and supplements qi, nourishes the blood for tranquilization of spirit, alleviates the toxicity of drugs, and is used for weakness of spleen and stomach, reduced appetite and loose stool, blood-deficiency etiolation, and hysteria of woman.

Fruit of Chinese magnoliavine is sour in flavor and warm in nature, acts on lung, kidney, and heart, astringes lung, nourishes kidney, promotes the secretion of body fluid, constrains sweating, arrests seminal emission, and is used for kidney-deficiency asthma, mouth dryness and thirst, spontaneous perspiration, night sweating, internal lesion caused by overexertion and emaciation, wet dream and spermatorrhea, and chronic diarrhea and dysentery.

Lilium brownii is sweet in flavor and cold in nature, acts on heart and lung, nourishes yin and moistens lung, clears away the heart fire and calms mind, and is used for yin-deficiency irritating dry cough, over-strained cough and hemoptysis, dysphoria and pavor, insomnia and dreamful sleep, and trance.

Donkey-hide gelatin is neutral in nature and slightly sweet in flavor, acts on lung, liver, and kidney, replenishes blood and nourishes yin, moistens dryness, stops bleeding, and is used for blood-deficiency etiolation, vertigo and palpitation, dysphoria insomnia, and lung dryness cough.

The qi deficiency constitution is formed mainly because native endowment is deficient and after long-term eating disorder, emotional disorder, long illness and fatigue, oldness and weakness cause heart, lung, spleen and kidney damages. The oral paste of the present application is based on yin nourishment and dryness moistening, spleen tonification and stomach nourishment, blood nourishment and tranquillization, qi supplementation and transportation assistance. The various drugs provide supplement without stagnation.

With the multiple types of drug materials of large dosages, efficacies of the various drug materials generate a synergistic effect, with the functions of reinforcing qi and nourishing blood, and the qi deficiency constitution can be conditioned, so that people are vigorous with strong resistibility, and the occurrence of diseases is avoided. With the conditioning for such constitution, it is more targeted and will not create side effects, without harm to the human body at all, and can achieve certain efficacy of strengthening the body.

As shown in FIG. 1, the processing method for the Chinese herbal oral paste for conditioning qi deficiency constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1

A Chinese herbal oral paste for conditioning qi deficiency constitution includes the following components in parts by weight: 5 parts of heterophylly falsestarwort root, 4 parts of dangshen (*Codonopsis pilosula*), 5 parts of fuling, 3 parts of prepared liquorice root, 6 parts of root and vine of manyprickle acanthopanax, 6 parts of milkvetch root, 3 parts of dried tangerine peel, 2 parts of angelica, 2 parts of Chinese arborvitae kernel, 7 parts of lotus seeds, 5 parts of radix asparagi, 5 parts of danshen root, 6 parts of solomonseal rhizome, 7 parts of hyacinth bean, 6 parts of Chinese yam, 1 parts of villous amomum fruit, 3 parts of coix seed, 6 parts of glossy ganoderma, 3 parts of finger citron, 5 parts of Chinese dates, 3 parts of fruit of Chinese magnoliavine, 13 parts of lilium brownii, 20 parts of xylitol, and 30 parts of donkey-hide gelatin.

The processing method therefor includes the following steps in sequence:

preparation of materials: measuring raw materials of formula ratio according to composition of the Chinese herbal oral paste, and washing raw materials, except donkey-hide gelatin and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering drug juice with gauze, then soaking filtered dregs of decoction with clear water and decocting the soaked dregs of decoction with low heat for 1 hour, thus repeating 4 times, thencombining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol and melted donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 2

A Chinese herbal oral paste for conditioning qi deficiency constitution includes the following components in parts by weight: 16 parts of heterophylly falsestarwort root, 15 parts of dangshen (*Codonopsis pilosula*), 16 parts of fuling, 7 parts of prepared liquorice root, 17 parts of root and vine of manyprickle acanthopanax, 18 parts of milkvetch root, 9 parts of dried tangerine peel, 14 parts of angelica, 8 parts of Chinese arborvitae kernel, 17 parts of lotus seeds, 16 parts of radix asparagi, 16 parts of danshen root, 17 parts of solomonseal rhizome, 15 parts of hyacinth bean, 20 parts of Chinese yam, 5 parts of villous amomum fruit, 17 parts of coix seed, 18 parts of glossy ganoderma, 10 parts of finger citron, 14 parts of Chinese dates, 9 parts of fruit of Chinese magnoliavine, 25 parts of lilium brownii, 40 parts of xylitol, and 50 parts of donkey-hide gelatin.

The processing method therefor includes the following steps in sequence:

preparation of materials: measuring raw materials of formula ratio according to composition of the Chinese herbal oral paste, and washing raw materials, except donkey-hide gelatin and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering drug juice with gauze, then soaking filtered dregs of decoction with clear water and decocting the soaked dregs of decoction with low heat for 1 hour, thus repeating 4 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol and melted donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 3

A Chinese herbal oral paste for conditioning qi deficiency constitution includes the following components in parts by weight: 7 parts of heterophylly falsestarwort root, 7 parts of dangshen (*Codonopsis pilosula*), 7 parts of fuling, 4 parts of prepared liquorice root, 9 parts of root and vine of manyprickle acanthopanax, 9 parts of milkvetch root, 5 parts of dried tangerine peel, 6 parts of angelica, 4 parts of Chinese arborvitae kernel, 10 parts of lotus seeds, 7 parts of radix asparagi, 7 parts of danshen root, 9 parts of solomonseal rhizome, 10 parts of hyacinth bean, 10 parts of Chinese yam, 2 parts of villous amomum fruit, 9 parts of coix seed, 9 parts of glossy ganoderma, 5 parts of finger citron, 7 parts of Chinese dates, 5 parts of fruit of Chinese magnoliavine, 16 parts of lilium brownii, 25 parts of xylitol, and 35 parts of donkey-hide gelatin.

The processing method therefor includes the following steps in sequence:

preparation of materials: measuring raw materials of formula ratio according to composition of the Chinese herbal oral paste, and washing raw materials, except donkey-hide gelatin and xylitol, for subsequent use;

soaking: soaking the cleaned raw materials with 9 folds of water for 12 h, with the water over the raw materials by 13 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol and melted donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 4

A Chinese herbal oral paste for conditioning qi deficiency constitution includes the following components in parts by weight: 13 parts of heterophylly falsestarwort root, 13 parts of dangshen (*Codonopsis pilosula*), 13 parts of fuling, 6 parts of prepared liquorice root, 14 parts of root and vine of manyprickle acanthopanax, 15 parts of milkvetch root, 7 parts of dried tangerine peel, 10 parts of angelica, 7 parts of Chinese arborvitae kernel, 15 parts of lotus seeds, 13 parts of radix asparagi, 13 parts of danshen root, 13 parts of solomonseal rhizome, 13 parts of hyacinth bean, 16 parts of Chinese yam, 4 parts of villous amomum fruit, 15 parts of coix seed, 15 parts of glossy ganoderma, 7 parts of finger citron, 13 parts of Chinese dates, 7 parts of fruit of Chinese magnoliavine, 23 parts of lilium brownii, 35 parts of xylitol, and 45 parts of donkey-hide gelatin.

The processing method therefor includes the following steps in sequence:

preparation of materials: measuring raw materials of formula ratio according to composition of the Chinese herbal oral paste, and washing raw materials, except donkey-hide gelatin and xylitol, for subsequent use;

soaking: soaking the cleaned raw materials with 9 folds of water for 10 h, with the water over the raw materials by 17 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol and melted donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 5

A Chinese herbal oral paste for conditioning qi deficiency constitution includes the following components in parts by weight: 10 parts of heterophylly falsestarwort root, 10 parts of dangshen (*Codonopsis pilosula*), 10 parts of fuling, 5 parts of prepared liquorice root, 12 parts of root and vine of manyprickle acanthopanax, 12 parts of milkvetch root, 6 parts of dried tangerine peel, 8 parts of angelica, 6 parts of Chinese arborvitae kernel, 12 parts of lotus seeds, 10 parts of radix asparagi, 10 parts of danshen root, 12 parts of solomonseal rhizome, 12 parts of hyacinth bean, 13 parts of Chinese yam, 3 parts of villous amomum fruit, 12 parts of coix seed, 12 parts of glossy ganoderma, 6 parts of finger citron, 10 parts of Chinese dates, 6 parts of fruit of Chinese magnoliavine, 20 parts of lilium brownii, 30 parts of xylitol, and 40 parts of donkey-hide gelatin.

The processing method therefor includes the following steps in sequence:

preparation of materials: measuring raw materials of formula ratio according to composition of the Chinese herbal oral paste, and washing raw materials, except donkey-hide gelatin and xylitol, for subsequent use;

soaking: soaking the cleaned raw materials with 9 folds of water for 13 h, with the water over the raw materials by 18 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring and decocting and concentrating with low heat, until a drug liquid does not disperse when being dropped on paper, to obtain a vegetarian paste;

collecting an oral paste: pouring xylitol and melted donkey-hide gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Experiment Example 1

The Following is a Test for the Effects of the Chinese Herbal Oral Paste for Conditioning Qi Deficiency Constitution Prepared According to Embodiment 5 of the Present Disclosure Basic conditions of cases: 100 clinical cases of qi deficiency constitution, including 50 males and 50 females. The youngest was aged 12, and the oldest was aged 57.

Usage and dosage: 25 g each time, once a day. Brew 25 g of the oral paste with boiling water in a cup, and stir the oral paste to make it melt for administration.

The evaluation criteria for therapeutic effects:

Cured: the clinical symptoms completely disappeared, and normal life was restored.

Effective: the clinical symptoms partially disappeared, and various signs were gradually improved.

Ineffective: the symptoms and signs were not obviously improved.

Result statistics: 58 cases cured, effective to 34 cases, and ineffective to 8 cases, i.e., effective to 92 cases in total, therefore the total effective rate was 92%.

Experiment Example 2

In order to demonstrate that the Chinese herbal oral paste prepared by the present disclosure have unexpected technical effects on qi deficiency symptoms, an experiment was conducted on a product prepared by the present disclosure by using qi-deficiency models prepared by a swimming strain method in combination with a controlled feeding method, so as to demonstrate the remarkable therapeutic effects of the product of the present disclosure, and demonstrate the prominently advantageous technical effects achieved by the present disclosure. The specific experiment was as follows:

1. Experimental animals:

SD rats, half males and half females, with the body weight of 220-250 g.

2. Product for experiment

The Chinese herbal oral paste prepared according to Embodiments 1-5 of the present application.

3. Experimental method 3.1 Preparation of models

The rats were randomly divided into a normal group, a qi-deficiency model group, and five experimental groups of Embodiments 1-5. The normal group was normally fed, and had free access to food and drink, and the other groups were fed in a controlled manner (the feeding amount was half that of normal feeding) and conducted exhaustive swimming with the water temperature being controlled at 20° C. When the rats were swimming, they were prevented from resting by using tails to support their bodies at the bottom of the pool, and the swimming was conducted once a day for 14 days continuously, until they sank at the time of swimming and were still unable to return to the water surface 10 seconds later, this state was the so-called "exhausted". After the preparation of the models, the activities and the state of the rats in each group were observed. After the experiment was completed, 3% of pentobarbital sodium was administered to the rats by intraperitoneal injection for anesthesia, and 6-7 ml of blood was taken from the abdominal aorta of each rat, and was placed in a heparin anticoagulant tube for the detection of hemorrheological index.

3.2 Experimental group-division

The rats were randomly divided into seven groups, including a normal group, a qi-deficiency model group, and experimental groups of Embodiments 1-5, with ten rats in each group. The experimental groups of Embodiments 1-5 of the present disclosure were intragastrically administered with the Chinese herbal oral paste products prepared in Embodiments 1-5 of the present application, respectively (dosage: 0.4 g/kg), and the normal group was intragastrically administered with equivalent amount of saline for 14 days continuously.

3.3 Statistical analysis

SPSS12.0 software was used for statistics, the method of one-way analysis of variance was adopted, and analysis of variance was used for intergroup comparison. $P<0.05$ means that the difference has the statistical significance.

4. Behavioral study

Monitoring of the general condition: the state, activities, etc. of the model animals were observed, and scoring was carried out according to the specific characterizations thereof with reference to the scoring table of Table 1. The scoring results are shown in Table 2.

TABLE 1

Experimental Rats Biological Characterization Semi-quantitative Scoring Observation Table

| Score | State | Skin and Hair | Color of Ear and Tail | Stool |
|---|---|---|---|---|
| 0 | active | skin being tightly linked with fat, and elastic, hair being bright and supple | red and shiny | dry and formed stool |
| 1 | slightly unresponsive and having reduced locomotor activity | skin being slightly flabby with reduced skin turgor, and hair being dry, yellow and matt | light red and matt | sticky, soft and formed stool |
| 2 | lassitude and sluggish | skin being flabby, fat increasing, and hair being dry or tangled | slightly white and matt | formless and loose stool with a bad smell |
| 3 | listless with weakened confrontational activities | skin being flabby, becoming obese, hair being yellow and thin, and shedding | pale or pale with cyan | greenish-brown, loose and sticky stool with a foul smell |

TABLE 2

Experimental Rats Biological Characterization Observation Table

| Group | n | Score |
|---|---|---|
| Blank Group | 20 | 1.26 ± 0.37 |
| Model Group | 20 | 4.44 ± 0.63** |
| Embodiment 1 | 20 | 1.28 ± 0.29## |
| Embodiment 2 | 20 | 1.35 ± 0.30## |
| Embodiment 3 | 20 | 1.29 ± 0.54## |
| Embodiment 4 | 20 | 1.37 ± 0.38## |
| Embodiment 5 | 20 | 1.30 ± 0.42## |

Note:
compared with the blank group, **$P < 0.01$;
and compared with the model group, ##$P < 0.01$.

As can be seen from Table 2, the biological representation scoring experiment results of the rats in each group show that the rats in the blank control group are active and responsive; the rats in the qi-deficiency model group are lassitude, listless, sluggish and even squint; with flabby skin and matt hair on the back; with slightly white and dry tail and nose; and have loose but formed stool. Compared with the blank control group, the biological representation score is remarkably increased ($P<0.01$); and the biological representation scores of the rats administered with the Chinese herbal oral paste of Embodiments 1-5 of the present application are significantly different ($P<0.01$) from that of the model group.

5. In this experiment, the exhaustive swimming time of the rats in each group was further measured. The time experiment results show that, compared with the blank control group, the exhaustive swimming time of the rats in the qi-deficiency model group is remarkably reduced and has a statistically significant difference ($P<0.01$); and compared with the qi-deficiency model group, the exhaustive swimming time of the rats in the experimental groups of Embodiments 1-5 of the present disclosure is remarkably increased and has a statistically significant difference ($P<0.01$).

6. In this experiment, hemorrheological index was further tested for the rats in each group. The experimental results show that, compared with the model group, high shear blood viscosity, middle shear blood viscosity, low shear blood viscosity, plasma viscosity, fibrinogen, and erythrocyte deformation index and aggregation index in the experimental groups of Embodiments 1-5 of the present disclosure have been improved to different extents ($P<0.01$ or $P<0.05$).

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can be effective as sustained release, and a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

The invention claimed is:

1. A Chinese herbal oral paste for conditioning qi deficiency constitution, comprising the following components in parts by weight: 5-16 parts of heterophylly falsestarwort root, 4-15 parts of dangshen, 5-16 parts of fuling, 3-7 parts of prepared liquorice root, 6-17 parts of root and vine of manyprickle acanthopanax, 6-18 parts of milkvetch root, 3-9 parts of dried tangerine peel, 2-14 parts of angelica, 2-8 parts of Chinese arborvitae kernel, 7-17 parts of lotus seeds, 5-16 parts of radix asparagi, 5-16 parts of danshen root, 6-17 parts of solomonseal rhizome, 7-15 parts of hyacinth bean, 6-20 parts of Chinese yam, 1-5 parts of villous amomum fruit, 3-17 parts of coix seed, 6-18 parts of glossy ganoderma, 3-10 parts of finger citron, 5-14 parts of Chinese dates, 3-9 parts of fruit of Chinese magnoliavine, 13-25 parts of lilium brownii, 20-40 parts of xylitol, and 30-50 parts of donkey-hide gelatin.

2. The Chinese herbal oral paste for conditioning qi deficiency constitution of claim 1, wherein the heterophylly falsestarwort root is 7-13 parts by weight, the dangshen is 7-13 parts by weight, the fuling is 7-13 parts by weight, the prepared liquorice root is 4-6 parts by weight, the root and vine of manyprickle acanthopanax are 9-14 parts by weight, the milkvetch root is 9-15 parts by weight, the dried tangerine peel is 5-7 parts by weight, the angelica is 6-10 parts by weight, the Chinese arborvitae kernel is 4-7 parts by weight, the lotus seeds are 10-15 parts by weight, the radix asparagi is 7-13 parts by weight, the danshen root is 7-13 parts by weight, the solomonseal rhizome is 9-13 parts by weight, the hyacinth bean is 10-13 parts by weight, the Chinese yam is 10-16 parts by weight, the villous amomum fruit is 2-4 parts by weight, the coix seed is 9-15 parts by weight, the glossy ganoderma is 9-15 parts by weight, the finger citron is 5-7 parts by weight, the Chinese dates is 7-13 parts by weight, the fruit of Chinese magnoliavine is 5-7 parts by weight, the lilium brownii is 16-23 parts by weight, the xylitol is 25-35 parts by weight, and the donkey-hide gelatin is 35-45 parts by weight.

3. The Chinese herbal oral paste for conditioning qi deficiency constitution of claim 1, wherein the heterophylly falsestarwort root is 10 parts by weight, the dangshen is 10 parts by weight, the fuling is 10 parts by weight, the prepared liquorice root is 5 parts by weight, the root and vine of manyprickle acanthopanax are 12 parts by weight, the milkvetch root is 12 parts by weight, the dried tangerine peel is 6 parts by weight, the angelica is 8 parts by weight, the Chinese arborvitae kernel is 6 parts by weight, the lotus seeds are 12 parts by weight, the radix asparagi is 10 parts by weight, the danshen root is 10 parts by weight, the solomonseal rhizome is 12 parts by weight, the hyacinth bean is 12 parts by weight, the Chinese yam is 13 parts by weight, the villous amomum fruit is 3 parts by weight, the coix seed is 12 parts by weight, the glossy ganoderma is 12 parts by weight, the finger citron is 6 parts by weight, the Chinese dates is 10 parts by weight, the fruit of Chinese magnoliavine is 6 parts by weight, the lilium brownii is 20 parts by weight, the xylitol is 30 parts by weight, and the donkey-hide gelatin is 40 parts by weight.

4. A processing method for the Chinese herbal oral paste for conditioning qi deficiency constitution of claim 1, comprising the following steps in sequence: preparation of materials, soaking, decoction, concentration, and collecting an oral paste.

5. The processing method for the Chinese herbal oral paste for conditioning qi deficiency constitution of claim 4, wherein the step of preparation of materials is: measuring raw materials of formula ratio according to composition of the Chinese herbal oral paste, and washing raw materials, except donkey-hide gelatin and xylitol, for subsequent use.

6. The processing method for the Chinese herbal oral paste for conditioning qi deficiency constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning qi deficiency constitution of claim 6, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for conditioning qi deficiency constitution of claim 7, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

9. The processing method for the Chinese herbal oral paste for conditioning qi deficiency constitution of claim 8, wherein the step of collecting an oral paste is: pouring xylitol and melted donkey-hide gelatin into the vegetarian paste respectively, stirring them continuously with a shovel while cooking them slowly with low heat, until the juice can coagulate and not disperse into beads when being dropped into clear water, then canning the resulted oral paste.

10. The processing method for the Chinese herbal oral paste for conditioning qi deficiency constitution of claim 9, wherein the melting step is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

11. A processing method for the Chinese herbal oral paste for conditioning qi deficiency constitution of claim 2, comprising the following steps in sequence: preparation of materials, soaking, decoction, concentration, and collecting an oral paste.

12. The processing method for the Chinese herbal oral paste for conditioning qi deficiency constitution of claim 11, wherein the step of preparation of materials is: measuring raw materials of formula ratio according to composition of the Chinese herbal oral paste, and washing raw materials, except donkey-hide gelatin and xylitol, for subsequent use.

13. The processing method for the Chinese herbal oral paste for conditioning qi deficiency constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning qi deficiency constitution of claim 13, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for conditioning qi deficiency constitution of claim 14, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

16. The processing method for the Chinese herbal oral paste for conditioning qi deficiency constitution of claim 15, wherein the step of collecting an oral paste is: pouring xylitol and melted donkey-hide gelatin into the vegetarian paste respectively, stirring them continuously with a shovel while cooking them slowly with low heat, until the juice can coagulate and not disperse into beads when being dropped into clear water, then canning the resulted oral paste.

17. The processing method for the Chinese herbal oral paste for conditioning qi deficiency constitution of claim 16, wherein the melting step is: smashing lumps of donkey-hide gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

18. A processing method for the Chinese herbal oral paste for conditioning qi deficiency constitution of claim 3, comprising the following steps in sequence: preparation of materials, soaking, decoction, concentration, and collecting an oral paste.

19. The processing method for the Chinese herbal oral paste for conditioning qi deficiency constitution of claim 18, wherein the step of preparation of materials is: measuring raw materials of formula ratio according to composition of the Chinese herbal oral paste, and washing raw materials, except donkey-hide gelatin and xylitol, for subsequent use.

20. The processing method for the Chinese herbal oral paste for conditioning qi deficiency constitution of claim 19, wherein the soaking step is: soaking the cleaned raw materials with 8-10 folds of water for 8-15 h, with the water over the raw materials by 10-20 cm.

\* \* \* \* \*